US007235665B2

(12) United States Patent
Schroeder et al.

(10) Patent No.: US 7,235,665 B2
(45) Date of Patent: Jun. 26, 2007

(54) PROCESS FOR THE PRODUCTION OF PIPERIDINE DERIVATIVES

(75) Inventors: Collin H. Schroeder, Madison, WI (US); Ryan R. Huddleston, Austin, TX (US); Richard H. Charles, Verona, WI (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 610 days.

(21) Appl. No.: 10/829,803

(22) Filed: Apr. 22, 2004

(65) Prior Publication Data

US 2004/0198983 A1   Oct. 7, 2004

Related U.S. Application Data

(62) Division of application No. 10/166,893, filed on Jun. 11, 2002, now Pat. No. 6,743,941.

(60) Provisional application No. 60/298,397, filed on Jun. 15, 2001.

(51) Int. Cl.
*C07D 211/22* (2006.01)
(52) U.S. Cl. ..................................... 546/239
(58) Field of Classification Search ................ 546/239
See application file for complete search history.

(56) References Cited

FOREIGN PATENT DOCUMENTS

| AT | 392782 | 6/1991 |
|---|---|---|
| DE | 2946809 A1 | 6/1981 |
| EP | 0347123 | 12/1989 |
| WO | WO95/00482 | 1/1995 |
| WO | WO93/21156 | 10/2003 |

OTHER PUBLICATIONS

Benigni "Methos of producing . . . " CA 111:173993 (1989).*
Kawai et al. "A Facile synthesis of . . . " J. Org. Chem. v.59 (1994) p. 2620-2622.*
Tacke et al. "Syntheses and pharmacological . . . " Organometallics v.23 (2004) p. 4915-4923.*
Bounaim et al, Ab Initio structural study and QSAR of certain Ibuprofen derivatives as possible antlinflamotory agents, Floia Chimica Theoretica Latina; (2000); 28(1-4); pp. 88-89.
Graul, A. et al., Faxofenadine Hydrochloride, Drugs of the Future, 1996, vol. 21, No. 10, pp. 1017-1021.
Hester, Jackson, B. et al., N-[(uomega-Amino-1-hydroxyalkyl)phenyl]methanesulfonamide Derivatives with Class III Antiarrhythmic Activity, J. Med. Chem., 1991, vol. 34, No. 1, pp. 308-315.
Smeyers et al, Conformational analysis of some .alpha.-phenylpropionic acids with anti-inflammatory activity, Journal of Pharmaceutical Sciences (1985); 74(10); pp. 47-49.

* cited by examiner

*Primary Examiner*—Celia Chang
(74) *Attorney, Agent, or Firm*—Ronald G. Ort

(57) ABSTRACT

The present invention relates to processes for preparing certain piperidine derivatives, including fexofenadine (F), the active ingredient in the non-sedating antihistamine sold in the U.S. under the designation "Allegra®". This invention also relates to novel synthetic intermediates useful in the processes of the present invention.

9 Claims, No Drawings

PROCESS FOR THE PRODUCTION OF PIPERIDINE DERIVATIVES

This application is a divisional of application Ser. No. 10/166,893, filed Jun. 11, 2002 now U.S. Pat. No. 6,743,941, which claims the benefit of U.S. Provisional Application No. 60/298,397, filed Jun. 15, 2001.

BACKGROUND OF THE INVENTION

The present invention relates to processes for preparing certain piperidine derivatives, including fexofenadine (F), the active ingredient in the non-sedating antihistamine sold in the U.S. under the designation "Allegra®". This invention also relates to novel synthetic intermediates useful in the processes of the present invention.

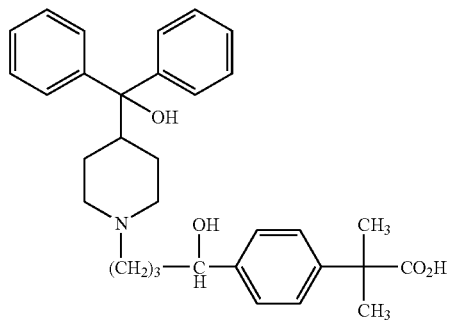

(F)

SUMMARY OF THE INVENTION

The present invention relates to processes for the preparation of piperidine derivatives of the formulas I, II, VI and VII:

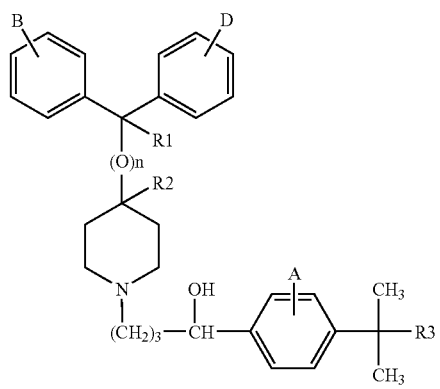

(I)

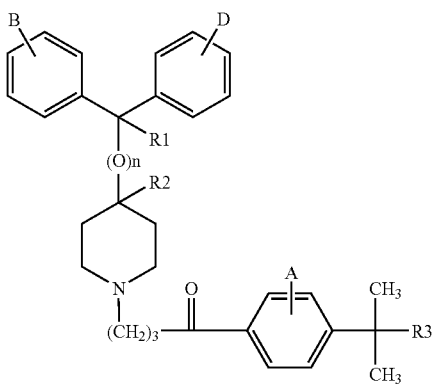

(II)

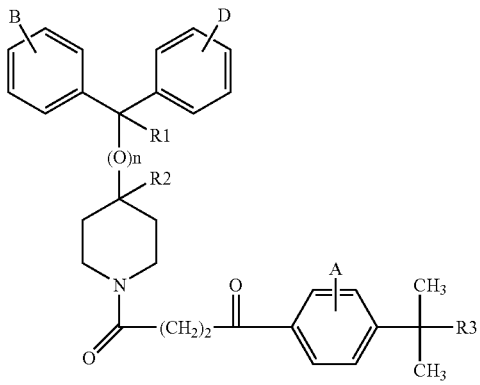

(VI)

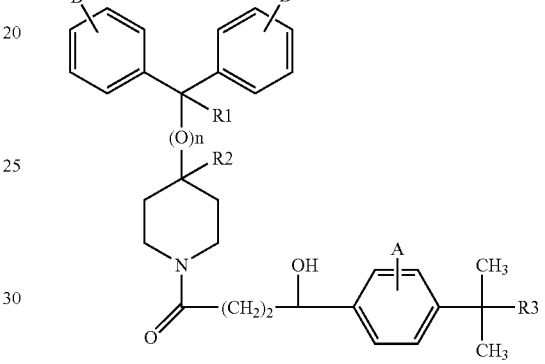

(VII)

wherein
  n is 0 or 1;
  R1 is hydrogen or hydroxy;
  R2 is hydrogen;
  R1 and R2 taken together form a double bond between the carbon atoms bearing R1 and R2;
  R3 is COOH, $CO_2$alkyl, $CH_2OH$, hydroxyl, protected hydroxyl, cyano, $CONH_2$, CONHalkyl or $CON(alkyl)_2$, wherein each of the alkyl groups contained in any of them contains from 1–6 carbon atoms
  A, B, and D may be substituents of their respective rings in the meta, para or ortho position and which may be different or the same and are hydrogen, halogens, alkyl, hydroxy, or alkoxy,
  and pharmaceutically acceptable salts thereof,
  with the proviso that where R1 and R2 are taken together to form a double bond between the carbon atoms bearing R1 and R2 or where R1 is hydroxy, n is 0.

The present invention also relates to novel synthetic intermediates for formulas III and IIIa, and VI which are useful in the preparation of the piperidine derivatives of formulas I, II, VI and VII:

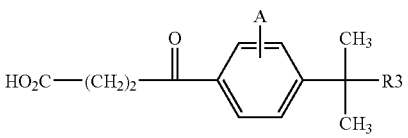

(III)

-continued (IIIa)

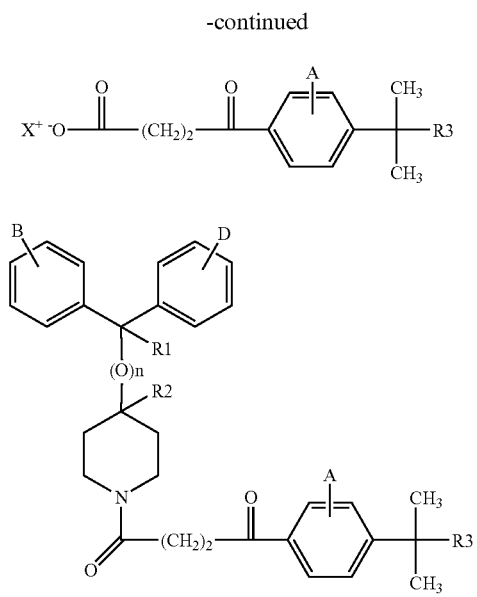

(VI)

wherein A, B, D, R1, R2, R3 and n are as previously defined and X⁺ is a Lewis Acid.

Although a wide variety of piperidine derivatives can be prepared by the process of the present invention, it is particularly useful for preparing fexofenadine (F), the active ingredient in the non-sedating antihistamine sold in the U.S. under the designation "Allegra®":

(F)

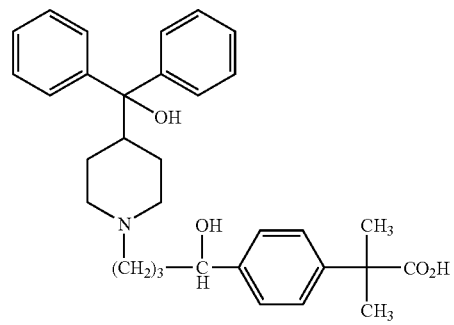

Thus, particularly preferred novel synthetic intermediates for use in the processes of the present invention which are useful in the preparation of the fexofenadine (F) are compounds of the formulas VIII, VIIIa, and IX:

(VIII)

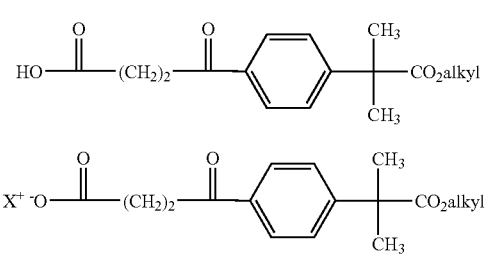

(VIIIa)

(IX)

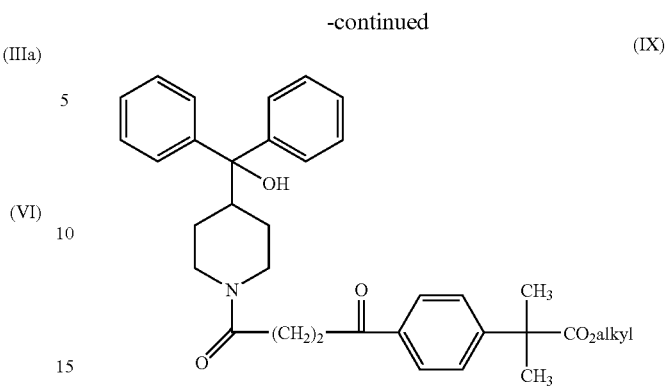

wherein alkyl is 1–6 carbon atoms and X⁺ is a Lewis acid.

The processes of the present invention for the preparation of piperidine derivatives of the formulas I, II, VI and VII comprise:

a) acylating a starting compound of the formula 19:

(19)

with a compound of the formula 18:

(18)

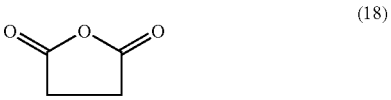

under conditions effective to produce a mixture of regioisomers of the formula XI:

(XI)

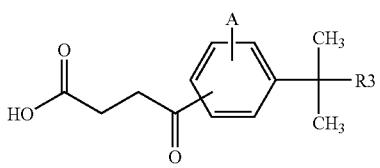

b) recovering from the mixture of regioisomers the compound of the formula III:

(III)

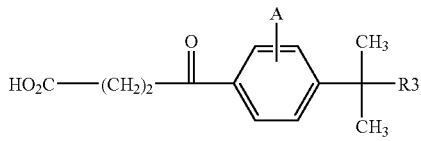

c) converting the compound of step b) to the piperidine derivative compound of the formula VI:

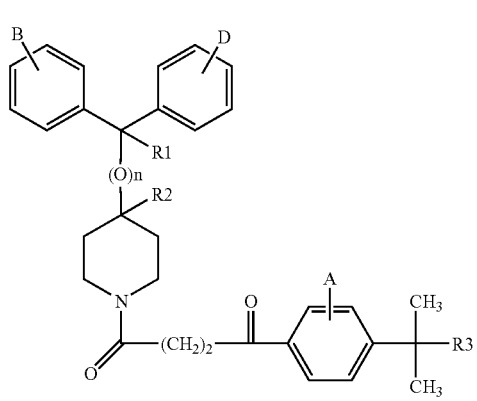

with a piperidine compound of the formula 17:

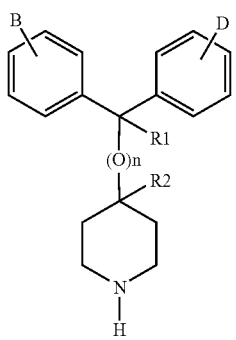

d) optionally reducing the piperidine derivative compound of step c) to give the compound of the formula I:

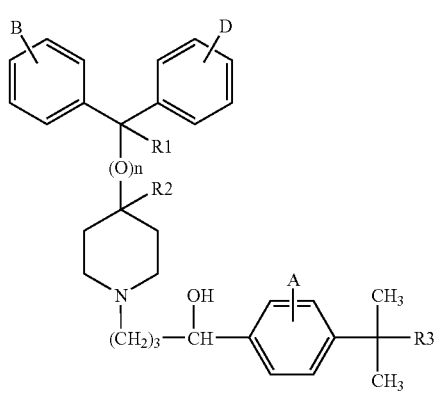

e) optionally reducing the piperidine derivative compound of step c) to give the piperidine derivative of the formula VII;

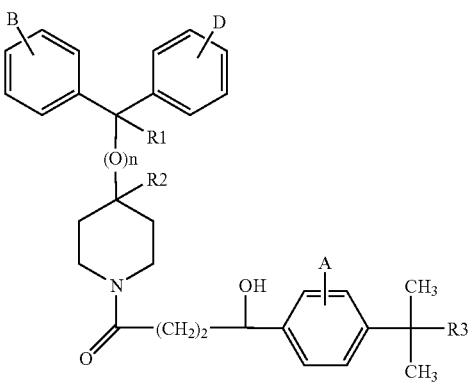

and f) optionally oxidizing the piperidine derivative of step d to give the piperidine derivative of formula II:

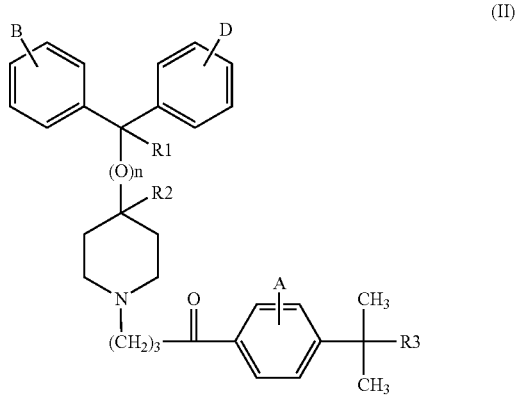

wherein all substituents are as previously defined.

Included within this process is a process for preparation of fexofenadine (F), the active ingredient in the non-sedating antihistamine sold in the U.S. under the designation "Allegra®", which comprises:

a) acylating a starting compound of the formula 21:

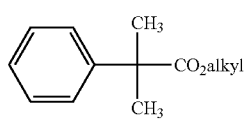

with a compound of the formula 20:

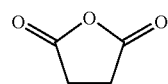

(18)

under conditions effective to produce a mixture of regioisomers of the formula 25:

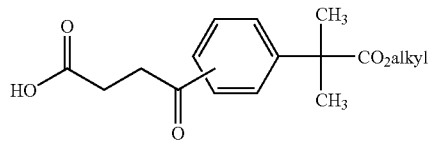

(25)

b) recovering from the mixture of regioisomers the compound of the formula VIII:

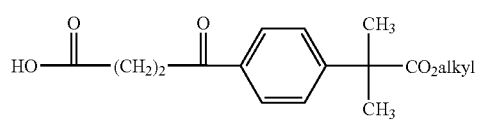

(VIII)

c) converting the compound of step b) to the piperidine derivative compound of the formula IX:

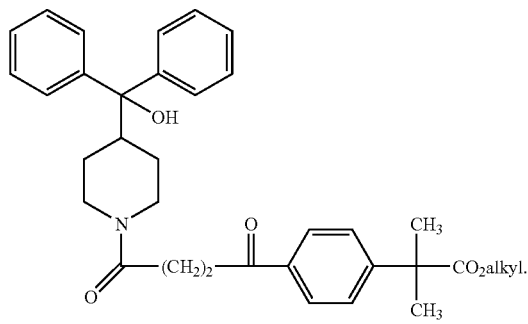

(IX)

with a piperidine compound of the formula 23:

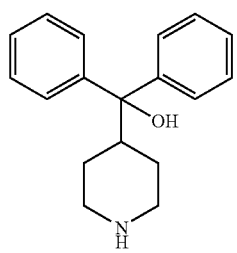

(23)

d) reducing the piperidine derivative compound of step c) to provide a piperidine derivative of the formula 24;

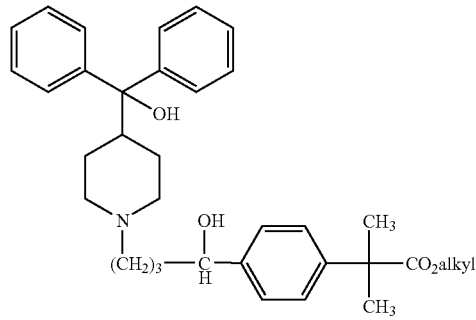

(24)

and e) converting the $CO_2$alkyl moiety of the piperidine derivative of formula 24 to a $CO_2H$ moiety to produce fexofenadine (F)

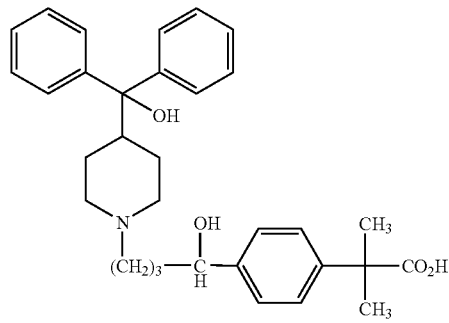

(F)

wherein alkyl is 1–6 carbon atoms.

DETAILED DESCRIPTION OF THE INVENTION

The present invention relates to a process for the preparation of piperidine derivatives of the formulas I, II, VI and VII:

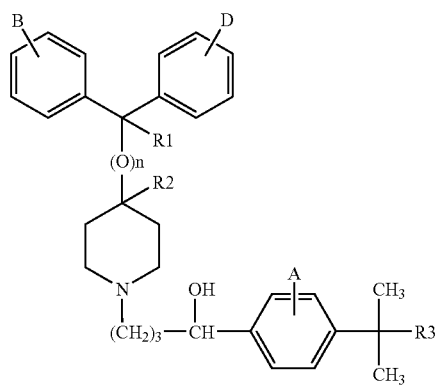

(I)

-continued

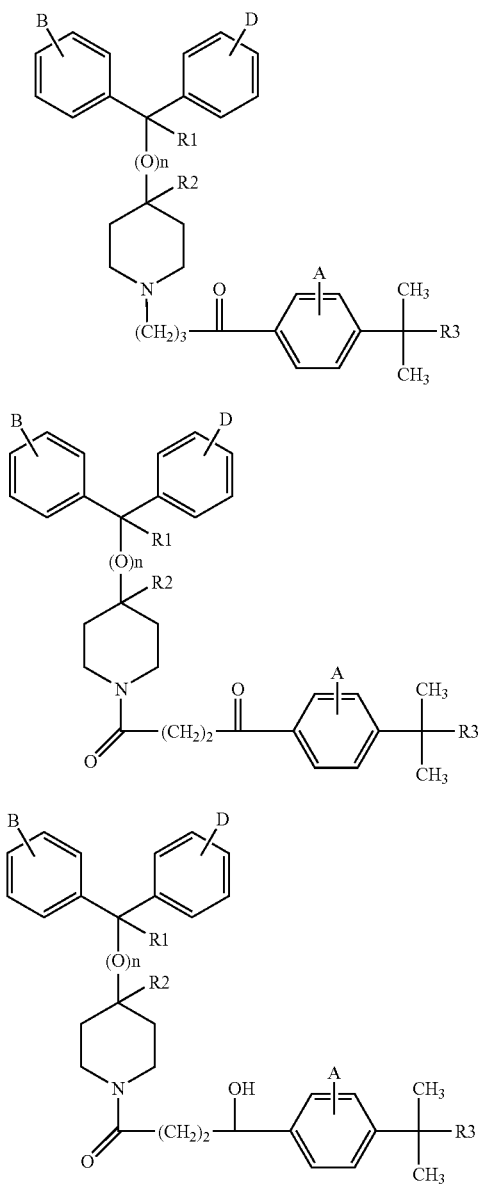

wherein
n is 0 or 1;
R1 is hydrogen or hydroxy;
R2 is hydrogen;
R1 and R2 taken together form a double bond between the carbon atoms bearing R1 and R2;
R3 is COOH, $CO_2$alkyl, $CH_2OH$, hydroxyl, protected hydroxyl, cyano, $CONH_2$, CONHalkyl or CON(alkyl)$_2$, wherein each of the alkyl groups contained in any of them contains from 1–6 carbon atoms A, B, and D may be substituents of their respective rings in the meta, para or ortho position and which may be different or the same and are hydrogen, halogens, alkyl, hydroxy, or alkoxy, and pharmaceutically acceptable salts thereof, with the proviso that where R1 and R2 are taken together to form a double bond between the carbon atoms bearing R1 and R2 or where R1 is hydroxy, n is 0.

The present invention also relates to novel intermediates of the formula II, IIIa, and VI:

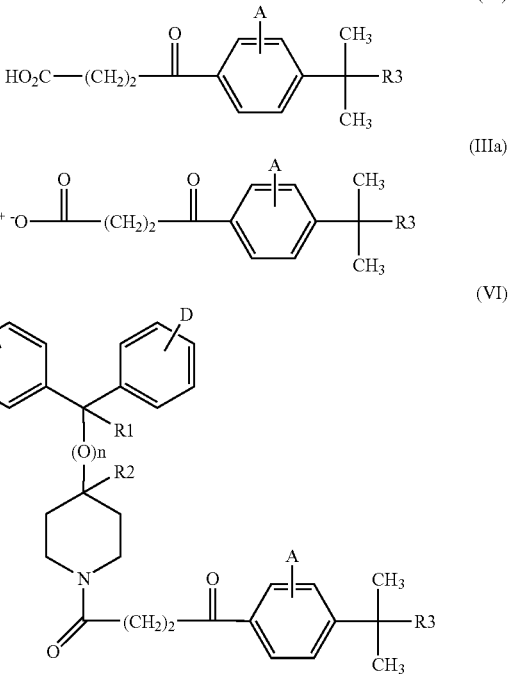

wherein A, B, D, R1, R2, R3 and n are as previously defined and $X^+$ is a Lewis Acid.

Although a wide variety of piperidine derivatives can be prepared by the process of the present invention, it is particularly useful for preparing fexofenadine (F), the active ingredient in the non-sedating antihistamine sold in the U.S. under the designation "Allegra®":

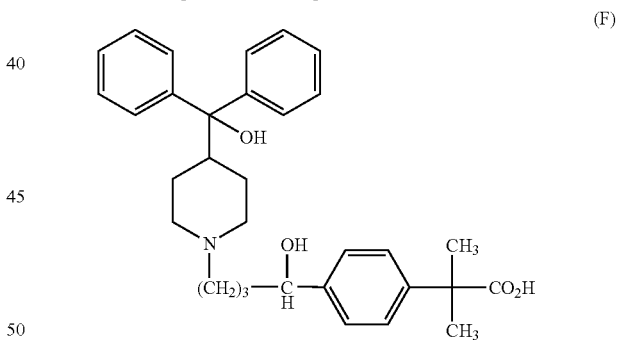

Thus, particularly preferred novel synthetic intermediates for use in the processes of the present invention which are useful in the preparation of the fexofenadine (F) are compounds of the formulas VII, VIIIa, and IX:

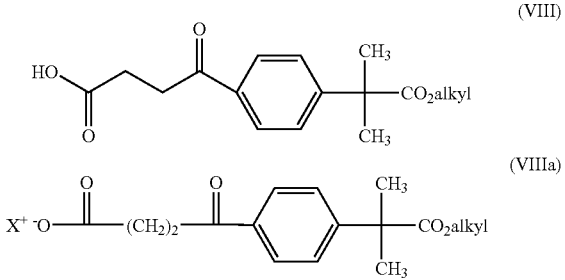

-continued

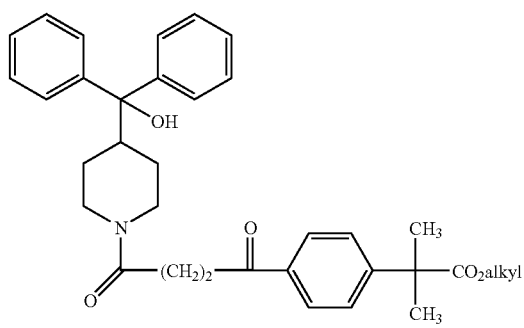
(IX)

wherein alkyl is 1–6 carbon atoms and X⁺ is a Lewis Acid.

The processes of the present invention for the preparation of piperidine derivatives of the formulas I, II, VI and VII comprise:

a) acylating a starting compound of the formula 19:

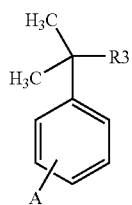
(19)

with a compound of the formula 18:

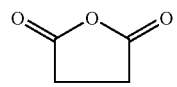
(18)

under conditions effective to produce a mixture of regioisomers of the formula XI:

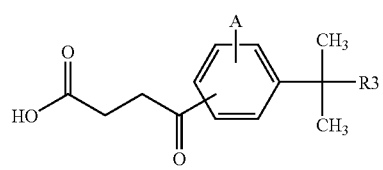
(XI)

b) recovering from the mixture of regioisomers the compound of the formula III:

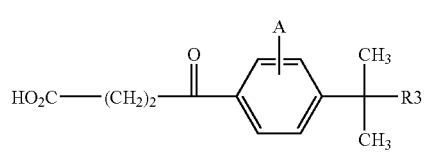
(III)

c) converting the compound of step b) to the piperidine derivative compound of the formula VI:

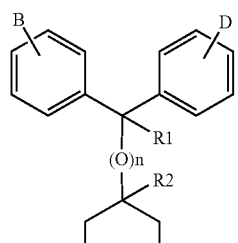
(VI)

with a piperidine compound of the formula 17:

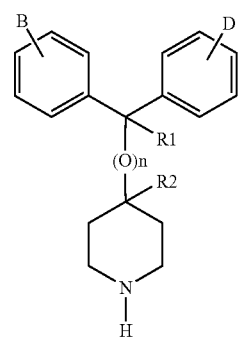
17 d) optionally reducing the piperidine derivative compound of step c) to give the compound of the formula I:

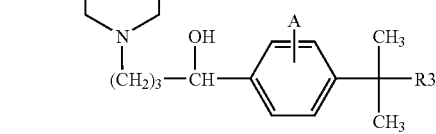
(I)

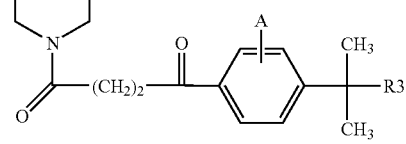

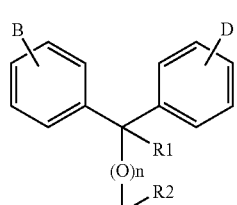

e) optionally reducing the piperidine derivative compound of step c) to give the piperidine derivative of the formula VII;

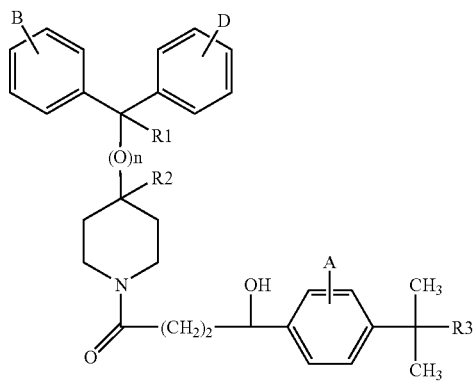

and f) optionally oxidizing the piperidine derivative of step d to give the piperidine derivative of formula II:

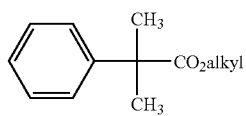

wherein all substituents are as previously defined.

Included within this process is a process for preparation of fexofenadine (F), the active ingredient in the non-sedating antihistamine sold in the U.S. under the designation "Allegra®", which comprises:

a) acylating a starting compound of the formula 21:

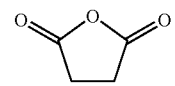

with a compound of the formula 18:

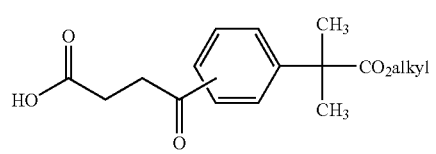

under conditions effective to produce a mixture of regioisomers of the formula 25:

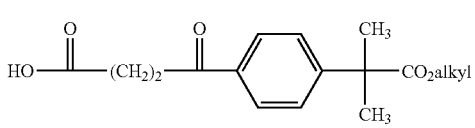

b) recovering from the mixture of regioisomers the compound of the formula VIII:

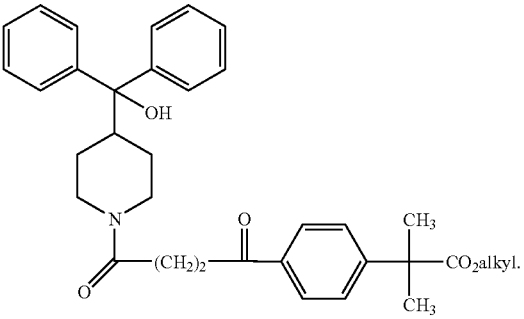

c) converting the compound of step b) to the piperidine derivative compound of the formula IX:

(IX)

with a piperidine compound of the formula 23:

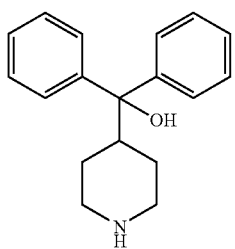

d) reducing the piperidine derivative compound of step c) to provide the piperidine derivative of formula 24; and

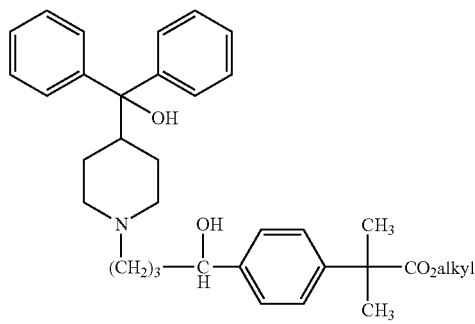

e) converting the $CO_2$alkyl moiety on the piperidine derivative of formula 24 to a $CO_2H$ moiety to produce fexofenadine (F)

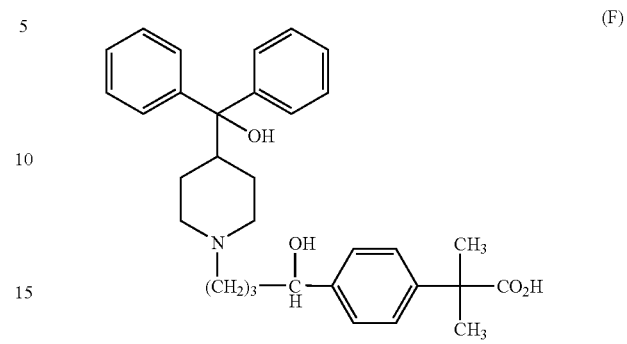

wherein alkyl is 1–6 carbon atoms.

This novel process for preparing the piperidine derivatives of formulas I, II, VI and VII and novel intermediates III, IIIa, and VI which are useful for preparing piperidine derivatives of formulas I, II, VI, and VII is outlined in Scheme A. In Scheme A, all substituents are as previously defined unless otherwise indicated.

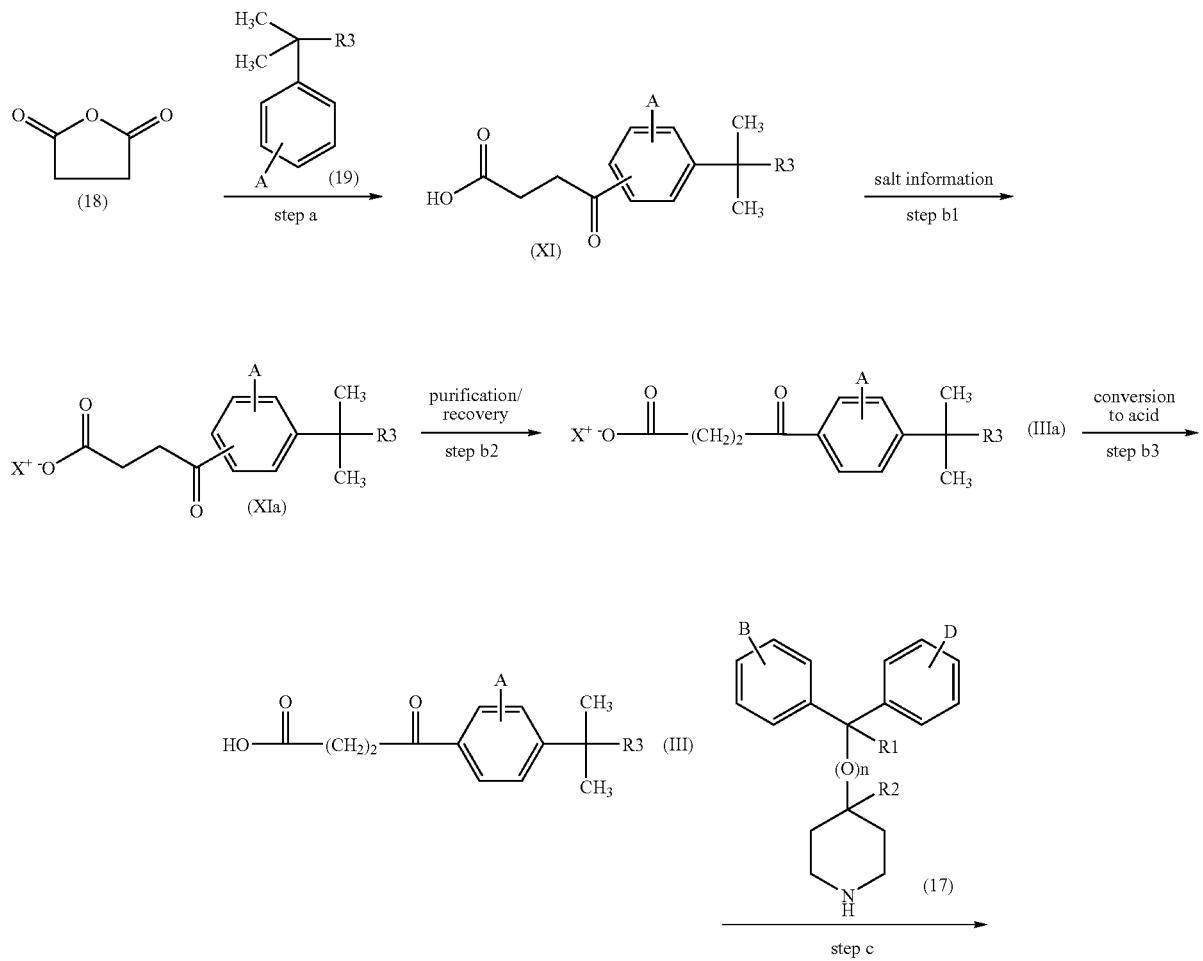

-continued

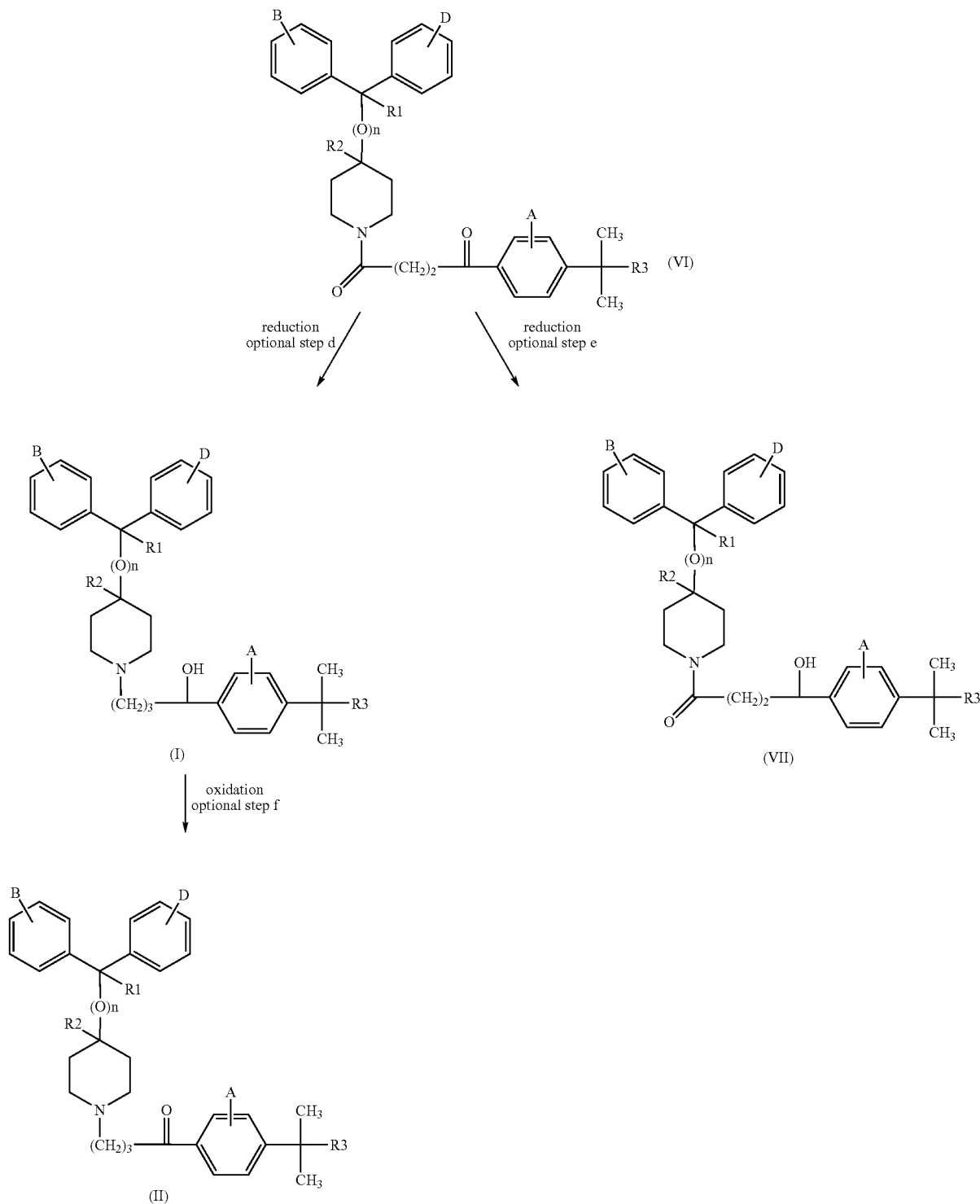

Scheme A provides general synthetic procedures for preparing the piperidine derivatives of formulas I, II, VI and VII and novel intermediates II, IIIa, and VI useful for preparing piperidine derivatives of formulas I, II, VI, and VII.

In step a, a starting compound of formula (19) is acylated with a dibasic acid anhydride of formula (18) under standard Friedel-Crafts conditions well known in the art, to produce a first mixture of regioisomers of formula XI, typically in a ratio of about 60% para, 40% meta isomers. Conditions for the acylation reaction of step a are those conventionally used in the Friedel-Crafts acylation reactions. Examples of compounds of formula (18) are substituted succinic anhydrides, glutaric anhydride, substituted glutaric anhydrides, polymeric anhydrides of higher dibasic acids, maleic anhydride, or substituted maleic anhydride.

For example, the acylation reaction of step a is catalyzed by a Lewis acid, such as AlCl$_3$, in an anhydrous aprotic solvent such as carbon disulfide, tetrachloethane, methylene chloride, nitrobenzene, or a mixture of anhydrous aprotic solvents. The reaction is typically carried out for a period of about 1 to about 18 hours, with about 12 to about 18 hours being preferred, at a temperature of about 0° C. to about the reflux temperature of the solvent utilized, with about 0° C. to about 25° C. being preferred.

In step b1, step b2, and step b3, the compound of formula III is recovered from the first mixture of regioisomers of formula XI. Such recovery is carried out by first, in step b1, forming the second mixture of regioisomeric salts of formula XIa:

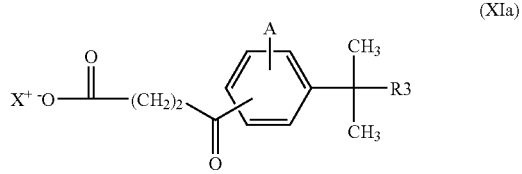

wherein X$^+$ is a Lewis acid and R3 and A are as previously defined; second, in step b2, crystallizing from the second mixture of regioisomeric salts of formula XIa, the salt of formula IIIa:

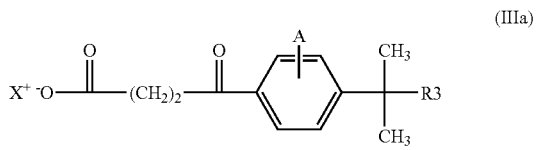

wherein X$^+$ is a Lewis acid and A and R3 is as previously defined. Such crystallization is carried out by fractional crystallization techniques known in the art. Suitable solvents for fractional crystallization include: alcohol solvents, like methanol, ethanol, isopropyl alcohol; ketone solvents, such as acetone or methyl ethyl ketone; ester containing solvents, like ethyl acetate or isopropyl acetate; ethereal solvents, like tetrahydrofuran; and acetonitrile. The preferred solvent is isopropyl alcohol. Suitable salts for fractional crystallization include alkali metal salts or preferably ammonium salts of the form NR$_{10}$R$_{11}$R$_{12}$, where R$_{10}$, R$_{11}$, and R$_{12}$ are hydrogen or a straight or branched alkyl of 1 to 6 carbon atoms which may be substituted at any position with a phenyl ring or a substituted phenyl ring. Of the salts of this form, phenethylamine is preferred. The pure regioisomer is isolated by filtration and in step b3, is converted to the free acid to give the compound of formula III by procedures well known in the art. Typically, this conversion is done by the treatment with acid.

In step c, the compound of formula III is coupled to a piperidine derivative of formula 17 under conditions effective to form the piperidine derivatives of formula VI. Such couplings are well known in the art. Generally, such procedures involve activating the free carboxyl group with reagents such as 1,3-dicyclohexylcarbodimide (DCC), 2-chloro-4,6-dimethoxy-1,3,5-triazine (CDMT), paranitrophenol, or as the acid chloride or mixed anhydride followed by addition of a primary or secondary amine. These reactions are carried out in an anhydrous aprotic solvent such as, ethyl acetate, methylene chloride, tetrahydrofuran or dimethylformamide with the preferred solvent being tetrahydrofuran. The reaction is typically carried out for a time of about 0.5 to about 12 hours, with about 2 to about 12 hours being preferred, at a temperature of about 0° C. to about the reflux temperature of the solvent utilized, with about 0° C. to about 25° C. being preferred.

In optional step d, the amido and keto moieties of the piperidine derivative of formula VI are reduced to give the piperidine derivative of formula I. Reduction can be carried out with the borane complexes such as, borane-methyl sulfide, borane-tetrahydrofuran in a suitable solvent. Alternatively, if the optically active derivative is desired, asymmetric reduction may be performed by addition of the appropriate catalyst such as, oxaborolidine based catalysts. The reduction is carried out in an anhydrous aprotic solvent, such as tetrahydrofuran or dioxane. The preferred solvent is tetrahydrofuran. The reduction is typically carried out at a temperature of from about 25° C. to about the reflux temperature of the solvent. Typical reaction times are from about 0.5 hours to about 48 hours, with about 12 to about 48 hours being preferred. The amino-borane complexes formed during reduction with the borane complexes are well known in the art and are typically broken by reaction of the complex with acid or by addition of TMEDA (N,N,N',N'-tetramethylethylenediamine) to the complex in ether, or through heating in protic media. This reaction is carried out in alcohol solvents, like methanol, ethanol, isopropyl alcohol. The preferred solvent is ethanol The reaction is carried out at a temperature ranging from 25° C. to the reflux temperature of the solvent and a reaction time of about 0.5 to about 24 hours, with about 12 to about 24 hours being preferred.

In optional step e, the keto moiety of the piperidine derivative of formula VI can be selectively reduced without affecting the amide moiety to give the piperidine derivative of formula VII. The selective reduction is typically done with sodium borohydride in lower alcohol solvents such as, methanol, ethanol, or isopropyl alcohol. The reaction is carried out at a temperature range of about 25° C. to about the reflux temperature of the solvent. Reaction times are typically about 0.5 hours to about 12 hours.

In optional step f, the hydroxy moiety of the piperidine derivative of formula I is oxidized to give the piperidine derivative of formula II.

This novel process as applied to the preparation of fexofenadine (F), the active ingredient in the non-sedating antihistamine sold in the U.S. under the designation "Allegra®" and novel intermediates VIII, VIIIa, and IX is outlined in Scheme B. In Scheme B, all substituents are as previously defined unless otherwise indicated.

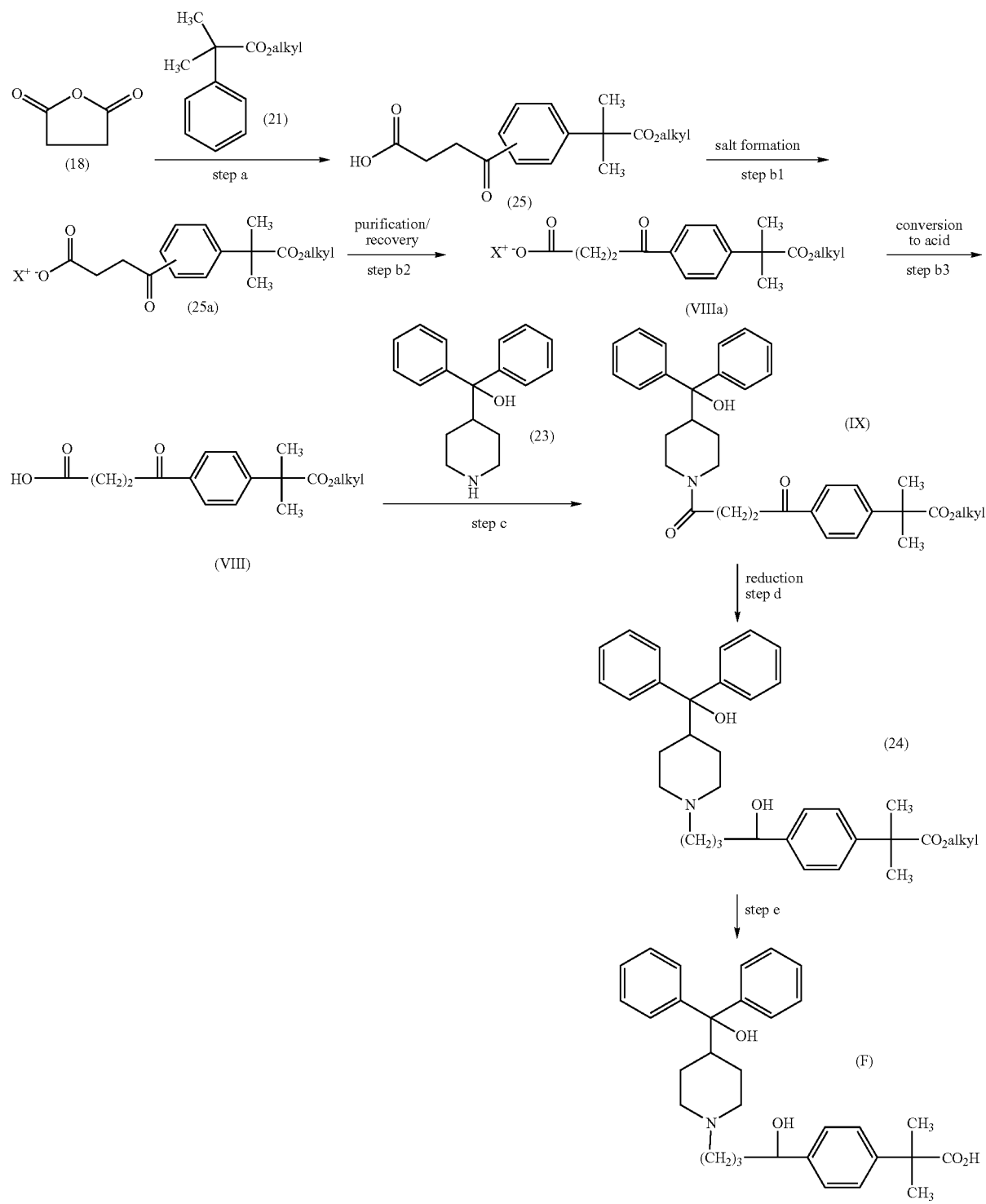

Scheme B

Scheme B provides a general synthetic procedure for preparing fexofenadine (F), the active ingredient in the non-sedating antihistamine sold in the U.S. under the designation "Allegra®" and novel intermediates VIII, VIIIa, and IX.

In step a, a starting compound of formula (21) is acylated with a succinic anhydride of formula (18) under standard Friedel-Crafts conditions well known in the art, to produce a first mixture of regioisomers of formula 25, typically in a ratio of about 60% para, 40% meta isomers. Conditions for the acylation reaction of step a are those conventionally used in the Friedel-Crafts acylation reactions.

For example, the acylation reaction of step a is catalyzed by a Lewis acid, such as AlCl$_3$, in an anhydrous aprotic solvent such as carbon disulfide, tetrachloroethane, methylene chloride, nitrobenzene, or a mixture of anhydrous aprotic solvents. The reaction is typically carried out for a period of about 1 to about 18 hours, with about 2 to about 18 hours being preferred, at a temperature of about 0° C. to about the reflux temperature of the solvent utilized, with about 0° C. to about 25° C. being preferred.

In step b1, step b2 and step b3, the compound of formula VII is recovered from the first mixture of regioisomers of formula 25. Such recovery is carried out by

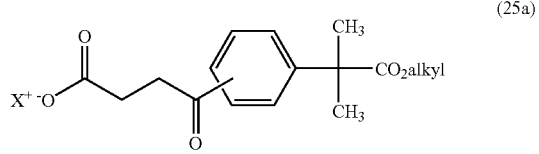

(25a)

first, in step b1, forming the second mixture of regioisomeric salts of formula 25a;

wherein X$^+$ is a Lewis acid and alkyl is as previously defined; second, in step b2, crystallizing from the second mixture of regioisomeric salts of formula 25a, the salt of formula VIIIa:

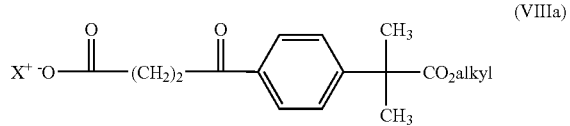

(VIIIa)

wherein X$^+$ is a Lewis acid and alkyl is as previously defined. Such crystallization is carried out by fractional crystallization techniques known in the art. Suitable solvents for fractional crystallization include: alcohol solvents, like methanol, ethanol, isopropyl alcohol; ketone solvents, such as acetone or methyl ethyl ketone; ester containing solvents, like ethyl acetate or isopropyl acetate; ethereal solvents, like tetrahydrofuran; and acetonitrile. The preferred solvent is isopropyl alcohol. Suitable salts for fractional crystallization include alkali metal salts or preferably ammonium salts of the form NR$_{10}$R$_{11}$R$_{12}$, where R$_{10}$, R$_{11}$, and R$_{12}$ are hydrogen or a straight or

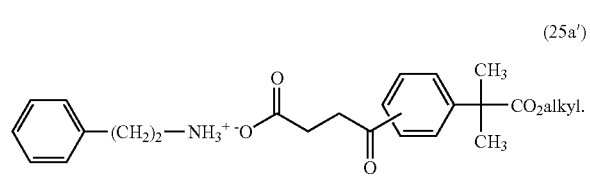

(25a')

branched alkyl of 1 to 6 carbon atoms which may be substituted at any position with a phenyl ring or a substituted phenyl ring. Of the salts of this form, phenethylamine is preferred, providing compounds of the formula 25a' after step b1 and compound of the formula VIIIa' after step b2:

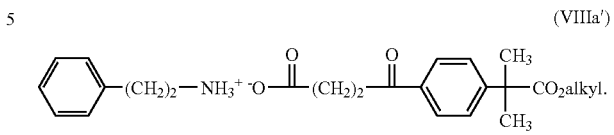

(VIIIa')

The pure regioisomer is isolated by filtration and in step b3, is converted to the free acid to give the compound of formula VII by procedures well known in the art. Typically, this conversion is done by the treatment with acid.

In step c, the compound of formula VII is coupled to a piperidine derivative of formula 23 under conditions effective to form the piperidine derivatives of formula IX. Such couplings are well known in the art. Generally, such procedures involve activating the free carboxyl group with reagents such as 1,3-dicyclohexylcarbodimide (DCC), 2-chloro-4,6-dimethoxy-1,3,5-triazine (CDMT), paranitrophenol, or as the acid chloride or mixed anhydride followed by addition of a primary or secondary amine. These reactions are carried out in an anhydrous aprotic solvent such as, ethyl acetate, methylene chloride, tetrahydrofuran or dimethylformamide with the preferred solvent being tetrahydrofuran. The reaction is typically carried out for a time of about 0.5 to about 12 hours, with about 2 to about 12 hours being preferred, at a temperature of about 0° C. to about the reflux temperature of the solvent utilized, with about 0° C. to about 25° C. being preferred.

In step d, the amido and keto moieties of the piperidine derivative of formula IX are reduced to give the piperidine derivative of formula 24. Reduction can be carried out with the borane complexes such as, borane-methyl sulfide, borane-tetrahydrofuran in a suitable solvent. Alternatively, if the optically active derivative is desired, asymmetric reduction may be performed by addition of the appropriate catalyst such as, oxaborolidine based catalysts. The reduction is carried out in an anhydrous aprotic solvent, such as tetrahydrofuran or dioxane. The preferred solvent is tetrahydrofuran. The reduction is typically carried out at a temperature of from about 25° C. to about the reflux temperature of the solvent. Typical reaction times are from about 0.5 to about 48 hours, with about 12 hours to about 48 hours being preferred. The amino-borane complexes formed during reduction with the borane complexes are well known in the art and are typically broken by reaction of the complex with acid, by addition of TMEDA (N,N,N',N'-tetramethylethylenediamine) to the complex in ether, or through heating in protic media This reaction is carried out in alcohol solvents, like methanol, ethanol, isopropyl alcohol The preferred solvent is ethanol. The reaction is carried out at a temperature ranging from 25° C. to the reflux temperature of the solvent and a reaction time of about 0.5 to about 24 hours, with about 12 to about 24 hours being preferred.

In step e, the ester moiety of the piperidine derivative of formula 24 is converted to the carboxylic acid by techniques and procedures well known to those in the art to give fexofenadine (F). For example, the ester moiety may be hydrolyzed using a suitable non-nucleophilic base, such as sodium methoxide in methanol as is known in the art. Other methods known in the art for ester cleavage include potassium carbonate in methanol, methanolic ammonia, potassium carbonate, potassium hydroxide, calcium hydroxide, sodium hydroxide, magnesium hydroxide, sodium hydroxide/pyridine in methanol, potassium cyanide in ethanol and sodium hydroxide in aqueous alcohols, with potassium hydroxide being preferred. The reaction is typically carried out in an aqueous lower alcohol solvent, such as methanol, ethanol, isopropyl alcohol, n-butanol, 2-ethoxyethanol or ethylene glycol or pyridine, at temperatures ranging from about room temperature to about the reflux temperature of the solvent, and the reaction time varies from about ½ hour to about 100 hours.

The following examples present typical syntheses as described in Schemes A and B. These examples are understood to be illustrative only and are not intended to limit the scope of the present invention in any way. As used herein, the following terms have the indicated meanings: "g" refers to grams; "mmol" refers to millimols; "mL" refers to milliliters; "bp" refers to boiling point; "mp" refers to melting point; "° C." refers to degrees Celsius; "mm Hg" refers to millimeters of mercury; "µL" refers to microliters; "µg" refers to micrograms; and "µM" refers to micromolar.

EXAMPLE 1

Scheme B, Step a: Preparation of 4-[4-(1-Methoxycarbonyl-1-methyl-ethyl)-phenyl]4-oxo-butyric acid and of 4-[3-(1-Methoxycarbonyl-1-methyl-ethyl)-phenyl]4-oxo-butyric acid (25)

Method 1:

Aluminum chloride (144 g, 1.08 moles) was added to 200 mL of carbon disulfide in a 1 L reaction kettle with stirring under a nitrogen atmosphere. The mixture was chilled to 0° C. to 5° C. after which time succinic anhydride (20) (26.0 g, 0.260 moles) was added in one portion. α,α-Dimethylphenylacetic acid methyl ester (21) (40.0 g, 0.224 moles) was added dropwise over 20 minutes to the reaction mixture. After addition, the ice-bath was removed and the mixture was allowed to warm to ambient temperature. After 2.75 hours, the carbon disulfide was decanted and discarded. The firm reaction product was placed (portionwise) into concentrated hydrochloric acid (150 mL) and crushed ice (1000 g). The product was extracted with ethyl acetate (2×400 mL) and washed with water (2×300 mL), brine (1×300 mL). The organic layer was dried over anhydrous magnesium sulfate, filtered and the ethyl acetate removed in vacuo to give a 60:40 (para:meta) mixture of the title compounds (25) as a light yellow oil.

Method 2:

Add succinic anhydride (20) (2 g, 0.050 moles) to a stirred solution of anhydrous methylene chloride (25 mL) and nitrobenzene (5 mL) under a nitrogen atmosphere. The reaction mixture was chilled to 0° C.–5° C. and aluminum chloride (20 g, 0.150 moles) was added in 5 g increments over 30 minutes. α,α-Dimethylphenylacetic acid methyl ester (21) (5.6 g, 0.031 moles) was added dropwise over 20 minutes to the reaction mixture. After 4 hours, the ice bath was removed and the reaction was allowed to proceed at room temperature for 16 hours. The reaction was quenched by slowly pouring into concentrated hydrochloric acid (50 mL) and crushed ice (300 g). Ethyl acetate (400 mL) was added with stirring. The organic phases were separated and washed with dilute brine (3×300 mL). The product was removed from the organic by extraction with saturated aqueous sodium bicarbonate (2×100 mL) containing brine (50 mL). The aqueous layer was acidified by slowly pouring into concentrated hydrochloric acid (50 ml) and ice (300 g). The product was recovered from the acidified reaction with ethyl acetate (200 mL). The organics were washed with water (400 mL), brine (100 mL), and dried over anhydrous sodium sulfate. Removal of the solvent in vacuo gave the title compounds (25) as a yellow oil (4.5 g, 0.016 moles), 80.4% yield.

Method 3:

Add succinic anhydride (16 g, 0.0160 moles) to anhydrous carbon disulfide (110 mL) with stirring under a nitrogen atmosphere. The reaction mixture was chilled to 0° C.–5° C. and aluminum chloride (72 g, 0.540 moles) was added in 18 g increments over 30 minutes. α,α-Dimethylphenylacetic acid methyl ester (21) (19.7 g, 0.111 moles) was added dropwise to the reaction mixture over 30 minutes. After 4 hours, the carbon disulfide was decanted from the insoluble reaction product, which was removed and carefully decomposed with concentrated hydrochloric acid (100 mL) and crushed ice (500 g). Ethyl acetate (600 mL) was added with stirring. The organic phases were separated and washed with dilute brine (3×400 mL). The product was removed as its sodium salt from the organic by extraction with saturated aqueous sodium bicarbonate (2×200 mL) containing brine (50 mL). The aqueous layer was acidified by slowly pouring into concentrated hydrochloric acid (100 mL) and ice (600 g). The product was recovered from the acidified reaction with ethyl acetate (300 mL). The organics were washed with water (2×300 mL), brine (200 mL), and dried over anhydrous sodium sulfate. Removal of the solvent in vacuo gave the title compounds (25) as a clear oil (22 g, 0.079 moles), 71.2% yield.

EXAMPLE 2

Scheme B, Step b1: Preparation of 4-[4-(1-Methoxycarbonyl-1-methyl-ethyl)-phenyl]-4-oxo-butyric acid phenethylamine salt and of 4-[3-(1-Methoxycarbonyl-1-methyl-ethyl)-phenyl]4-oxo-butyric acid phenethylamine salt (25a')

Method 1:

The mixture of 4-[4-(1-methoxycarbonyl-1-methylethyl)-phenyl]-4-oxo-butyric acid and of 4-[3-(1-methoxycarbonyl-1-methyl-ethyl)-phenyl]-4-oxo-butyric acid (25) from Example 1, Method 1 is dissolved in 150 mL of diethyl ether and cooled to 5° C. To the solution (assume 100% yield, 62.5 g, 0.224 moles) was added phenethylamine (28.5 g, 29.5 mL, 0.235 moles, 1.05 eq.) dropwise over 10 minutes. The suspension is placed in the freezer overnight. The insoluble phenethylamine salt is collected by vacuum filtration and rinsed with 75 mL of fresh cold diethyl ether to afford 72.0 g (80.5% yield over two steps—Example 1, Method 1 and Example 2, Method 1, 94.7% pure by HPLC) of the title compounds (25a') as a white solid.

Method 2:

To a solution of the 4-[4-(1-methoxycarbonyl-1-methylethyl)-phenyl]-4-oxo-butyric acid and of 4-[3-(1-methoxycarbonyl-1-methyl-ethyl)-phenyl]-4-oxo-butyric acid (25) from Example 1, Method 2 (22.0 g, 0.079 moles, 1.0 eq) in 100 mL of diethyl ether was added phenylethyl amine (10.5 g, 10.9 mL, 0.087 moles, 1.1 eq.). The insoluble phenethylamine salt is collected by vacuum filtration and rinsed with 25 mL of fresh diethyl ether to afford 30.0 g (95%) yield of the mixed isomer phenethylamine salts (25a').

EXAMPLE 3

Scheme B. Step b2: Preparation of 4-[4-(1-Methoxycarbonyl-1-methyl-ethyl)-phenyl]-4-oxo-butyric acid phenethylamine salt (VIIIa')

Method 1:
The mixture of 4-[4-(1-methoxycarbonyl-1-methyl-ethyl)-phenyl]-4-oxo-butyric acid phenethylamine salt and of 4-[3-(1-methoxycarbonyl-1-methyl-ethyl)-phenyl]-4-oxo-butyric acid phenethylamine salt (25a') obtained from Example 2, Method 1, (71.0 g) was crystallized from 2.1 L of hot isopropyl alcohol and collected by vacuum filtration to yield 36.9 g (52% yield) of a 91:9 (para:meta) isomeric mixture. The collected solid (36.9 g) was recrystallized from 1100 mL of hot isopropyl alcohol and collected by vacuum filtration to yield 30.0 g (81.3% yield, 42.3% overall yield based upon the original mixture, 70.4% total recovery of the para isomer) of 4-[4-33-(methoxycarbonyl-1-methyl-ethyl)-phenyl]-4-oxo-butyric acid phenethylamine salt (VIIIa'). (Note: For maximum yield and speed of crystallization, it is recommended that the solution is seeded with pure material after cooling to ambient temperature and then stored at −10° C.).

Method 2:
The mixture of 4-[4-(1-methoxycarbonyl-1-methyl-ethyl)-phenyl]-4-oxo-butyric acid phenethylamine salt and of 4-[3-(1-methoxycarbonyl-1-methyl-ethyl)-phenyl]-4-oxo-butyric acid phenethylamine salt (25a') obtained from Example 2, Method 2 (30.0 g) was crystallized from 1 liter of hot isopropyl alcohol and collected by vacuum filtration to yield 12.8 g (43% yield) of an 85:15 (para:meta) isomeric mixture. The collected solid (12.8 g) was recrystallized from 375 mL of hot isopropyl alcohol and collected by vacuum filtration to yield 10.2 g (80% yield, 34% overall yield based upon the original mixture) of the title compound (VIIIa').

EXAMPLE 4

Scheme B. Step b3: Preparation of 4-[4-(1-Methoxycarbonyl-1-methyl-ethyl)-phenyl]-4-oxo-butyric acid (VIII)

Method 1:
The 4-[4-(1-methoxycarbonyl-1-methyl-ethyl)-phenyl]-4-oxo-butyric acid phenethylamine salt (VIIIa') obtained from Example 3, Method 1 (30.0 g) was dissolved in 800 mL of warm water and acidified with concentrated hydrochloric acid to pH2. The aqueous layer was extracted with ethyl acetate (2×300 mL). The organics were washed with water (1×100 mL), brine (1×100 mL), dried over $MgSO_4$, filtered and concentrated in vacuo to 20.5 g (98.1% yield for conversion to the free acid) of the title compound (VIII) as a white crystalline solid (99.8% pure by HPLC). (Note: It is not necessary to isolate the salt as in Example 1. The crude oil from Example 1 can be dissolved into isopropyl alcohol directly, followed by the addition of phenethylamine. Crystallization occurs at −10° C., with a small reduction in overall yield.) $MH^+$ 279.2.

Method 2:
The 4-[4-(1-methoxycarbonyl-1-methyl-ethyl)-phenyl]4-oxo-butyric acid phenethylamine salt (VIIIa') obtained from Example 3, Method 2 (10.2 g) was dissolved in 200 mL of warm water and acidified with concentrated hydrochloric acid to pH2. The aqueous was extracted with ethyl acetate (2×150 mL). The organics were washed with water (1×50 mL), brine (1×50 mL), dried over MgSO4, filtered and concentrated in vacuo to give 6.8 g (96% yield) of the title compound (VIII) was a clear oil which solidified upon standing.

EXAMPLE 5

Scheme B, Step c: Preparation of 2-(4-{4-4-(Hydroxy-diphenyl-methyl)-piperidine-1-yl]-4-oxo-butyryl}-phenyl)-2-methyl-propionic acid methyl ester (IX)

Method 1:
The 4-[4-(1-Methoxycarbonyl-1-methyl-ethyl)-phenyl]-4-oxo-butyric acid (VIII) (20.0 g, 0.0719 mole) obtained from Example 4, Method 1 was dissolved in 250 mL of anhydrous tetrahydrofuran to which was added triethylamine (7.28 g, 10.02 mL, 0.0719 moles) in one portion. The flask containing the solution was placed in an ambient temperature water bath. To the solution was added ethyl chloroformate (7.02 g, 6.19 mL, 0.0647 mole) in THF (60 mL) dropwise over 1 minute. After addition, the mixture was allowed to stir at ambient temperature for 15 minutes. To the mixture was added α,α-diphenyl-4-piperidinomethanol (23) (19.2 g, 0.0719 moles) in THF (120 mL) over 2 minutes. The mixture was stirred at ambient temperature for 30 minutes. The solvent was removed under vacuum and the residue taken up in 600 mL of ethyl acetate. The organics were washed with water (1×200 mL), dilute acid (1×200 mL), ¼ saturated potassium carbonate (2×200 mL), water (1×200 mL), brine (1×200 mL), treated with $MgSO_4$, filtered, concentrated and dried under high vacuum to give the title compound (IX) as a white solid (29.2 g, 85.6% yield, 98.2% pure by HPLC). $MH^+$ 528.4.

Method 2:
The 4-[4-(1-Methoxycarbonyl-1-methyl-ethyl)-phenyl]-4-oxo-butyric acid (VIII) (20.0 g, 0.0719 mole) obtained from Example 4, Method 2 (6.8 g, 0.024 moles) and para-nitrophenol (6.7 g, 0.048 moles) was dissolved in ethyl acetate (300 mL) and cooled to 0° C. in an ice-bath. 1,3-Dicyclohexylcarbodiimide (9.9 g, 0.048 moles) was added to the chilled solution in one portion. The mixture is stirred at 0° C. for 1 hour and then allowed to warm to ambient temperature where the mixture is stirred for 7 hours. After than time azacyclonol (23) (7.1 g, 0.026 moles) is added to the mixture in one portion. The mixture is allowed to stir overnight for 15 hours. The reaction mixture is filtered through Whatman 541 paper to remove the precipitated 1,3-dicyclohexylurea. The filtrate is washed with ¼ saturated K2CO3 (3×100 mL), water (2×100 mL), dilute acid (1×100 mL), water (1×75 mL), brine (1×100 mL) and treated with MgSO4, filtered and concentrated to a yellow oil (10.9 g, 86% yield). The product is of sufficient purity to carry forward or if desired, a more pure sample can be obtained by crystallization from acetonitrile (6 ml/gram with ~80% recovery)

EXAMPLE 6

Scheme B, Step d: Preparation of 4-[4-[4-(Hydroxydiphenylmethyl)-1-piperidinyl]-1-hydroxybutyl]-α,α-dimethylbenzeneacetic acid methyl ester (24)

Method 1:
The 2-(4-{4-4-(Hydroxy-diphenyl-methyl)-piperidine-1-yl]4-oxo-butyryl}-phenyl)2-methyl-propionic acid methyl ester (IX) obtained from Example 5, Method 1 (28.0 g, 0.0531 mole) was dissolved in 300 mL of dry THF. To the stirred solution was added borane-methyl sulfide complex (0.136 moles, 12.92 mL) dropwise over five minutes. The mixture was heated at reflux for 60 minutes and then cooled to ambient temperature over 15 minutes. Methanol (200 mL) was added (initial 50 mL dropwise) and the mixture was stirred for 30 minutes. The mixture was concentrated under vacuum to give a white solid. The residue was dissolved in 300 mL of denatured ethanol and heated at reflux for 26 hours. The ethanol was removed in vacuo and the reaction product was taken up in ethyl acetate (1×500 mL). The organics were washed with water (3×200 mL), brine (1×200 mL) and treated with MgSO$_4$, filtered and concentrated in vacuo to give 26.4 g (96.6%, 91.0% pure by HPLC) of the title compound (24) as a white solid. MH$^+$ 516.6.

Method 2:

The 2-(4-{4-4-(Hydroxy-diphenyl-methyl)-piperidine-1-yl]-4-oxo-butyryl}-phenyl)-2-methyl-propionic acid methyl ester (IX) obtained from Example 5, Method 2 (5.28 g, 0.01 moles) was dissolved in 75 mL of dry THF. To the stirred solution was added borane-methyl sulfide complex (0.027 moles, 2.65 mL) dropwise over five minutes. The mixture was heated at reflux for 45 minutes and then cooled to ambient temperature. Methanol (40 mL) was added (slowly at first) and the mixture was stirred for 30 minutes. The solvents were removed in vacuo to give a solid, which was dissolved in ethyl acetate (500 mL) and washed with water (1×200 mL). ¼ saturated K$_2$CO$_3$ (1×200 mL), water (1×200 mL), brine (1×200 mL), treated with MgSO$_4$, filtered and concentrated in vacuo to a white solid. The white solid was dissolved in 60 mL of methanol to which was added 30 mL of 37% formaldehyde. The mixture was refluxed for 18 hours. The methanol was removed in vacuo (alternatively the reaction can be diluted 5 fold with water as a substitution of methanol removal) and the reaction product was extracted with ethyl acetate (2×150 mL). The organics were washed with water (2×100 mL), brine (1×100 mL) and treated with MgSO$_4$, filtered and concentrated in vacuo to give 4.7 g (91%) of the title compound (24) as a white solid of sufficient purity to carry forward.

EXAMPLE 7

Scheme B, Step e: Preparation of 4-[4-[4-(Hydroxydiphenylmethyl)-1-piperidinyl]-1-hydroxybutyl]-α,α-dimethylbenzeneacetic acid (F)

Method 1:

The 4-[4-[4-(Hydroxydiphenylmethyl)-1-piperidinyl]-1-hydroxybutyl]-α,α-dimethylbenzeneacetic acid methyl ester of Example 6, Method 1 (24) (20.0 g, 0.0388 mole) was dissolved in 200 mL of methanol. To the solution was added a sodium hydroxide solution (8.5 g in 85 mL water). The reaction mixture (cloudy at first then clears) was heated at reflux for 3 hours, and then cooled to ambient temperature. The solution was acidified to pH 4–5 with acetic acid (13.8 mL). The mixture was stirred at ambient temperature for 1.5 hours. The precipitate was collected by vacuum filtration and dried under vacuum to give 3.30 g (85% yield) of the title compound Fexofenadine (F) as a white solid. Purity assessment by HPLC 99.9%. Retention time and spectral match by HPLC against a fexofenadine standard. MH$^+$ 502.4

Method 2:

The 4-[4-[4-(Hydroxydiphenylmethyl)-1-piperidinyl]-1-hydroxybutyl]-α,α-dimethylbenzeneacetic acid methyl ester of Example 6, Method 2 (4.0 g, 0.0078 moles) was dissolved in 80 mL of methanol. To the solution was added a sodium hydroxide solution (2.8 g in 24 mL of water). The reaction mixture was heated at reflux for 3 hours, and then cooled to ambient temperature. The solution was acidified to pH 4–5 with acetic acid, followed by the addition of 40 mL of methanol. The mixture was stirred at ambient temperature for 1.5 hours. The precipitate was collected by vacuum filtration. The precipitate was dried under vacuum to give 3.3 g (85%) of the title compound fexofenadine (F) was a white solid. Purity assessment by HPLC 99.9%. Retention time and spectral match by HPLC against a fexofenadine standard. MH$^+$ 502.4

EXAMPLE 8

Scheme A. Optional Step f: Preparation of 4-[4-[4-(Hydroxydiphenylmethyl)-1-piperidinyl]-1-oxobutyl]-α,α-dimethylbenzeneacetic acid methyl ester 4-[4-[4-(Hydroxydiphenylmethyl)-1-piperidinyl]-1-hydroxybutyl]-α,α-dimethylbenzeneacetic acid methyl ester (2.05 g, 0.00398 mol) was dissolved in 100 mL of acetone and chilled in an ice-bath. To the solution was added Jones reagent (Prepared via the method of Feiser and Feiser) dropwise until a red color persisted. The reaction was allowed to warm to room temperature and then stirred for 18 hours at ambient temperature. The mixture was concentrated under vacuum to give a green solid. The residue was partitioned between ethyl acetate (150 mL) and water (150 mL). The organic layer was separated, washed with water (3×100 mL), brine (1×100 mL) and treated with MgSO$_4$, filtered and concentrated in vacuo to give a light green solid. Purification via column chromatography yielded 1.25 g (61% yield) of the title compound as a white solid. MH$^+$ 514.6.

We claim:

1. A compound of formula (IX):

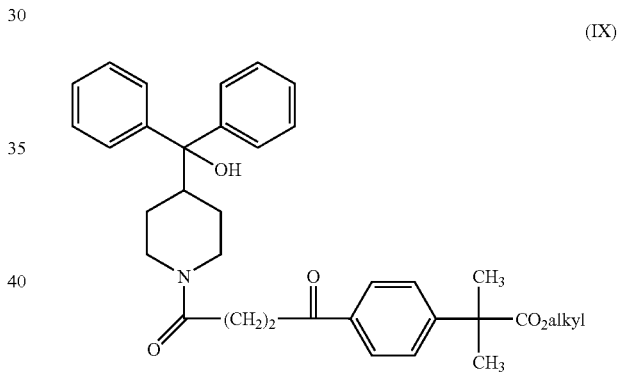

(IX)

wherein alkyl is 1–6 carbon atoms.

2. The compound of claim 1 wherein the alkyl is methyl.

3. The compound of claim 1 wherein the alkyl is ethyl.

4. The process for preparing a piperidine derivative compound of formula (IX):

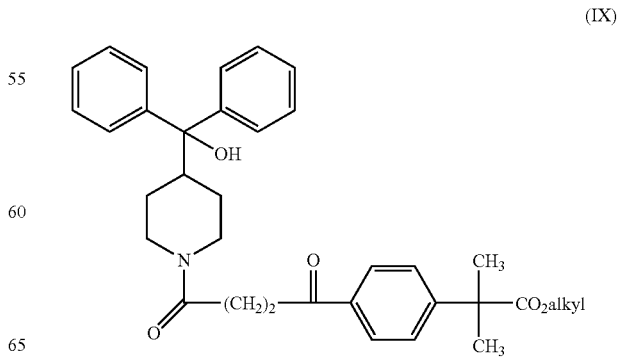

(IX)

wherein alkyl is 1–6 carbon atoms comprising providing a compound of formula (VIII):

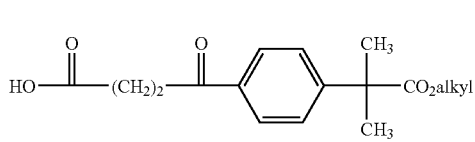
(VIII)

wherein alkyl is 1–6 carbon atoms, and converting the compound of formula (VIII) to the piperidine derivative compound of formula (IX) with a piperidine compound of formula (23):

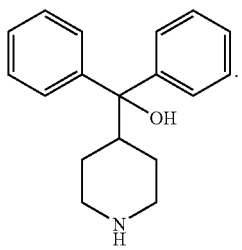
(23)

5. The process according to claim 4, wherein said providing comprises:

a) acylating a starting compound of formula (21):

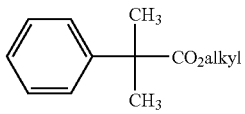
(21)

wherein alkyl is 1–6 carbon atoms with a compound of formula (18)

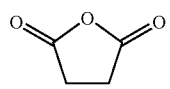
(18)

under conditions effective to produce a mixture of regioisomers of formula (25):

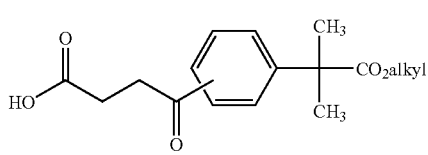
(25)

wherein alkyl is 1–6 carbon atoms; and b) recovering from the mixture of regioisomers the compound of formula (VIII):

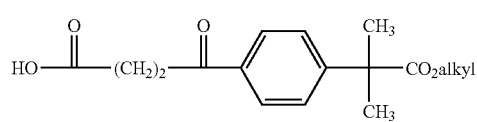
(VIII)

wherein alkyl is 1–6 carbon atoms.

6. The process according to claim 5 wherein said recovering comprises crystallizing a regioisomeric salt of formula (VIIIa):

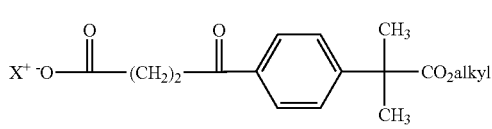
(VIIIa)

wherein alkyl is 1–6 carbon atoms and $X^+$ is a Lewis acid.

7. The process according to claim 6 wherein said recovering comprises crystallizing a regioisomeric salt of formula (VIIIa'):

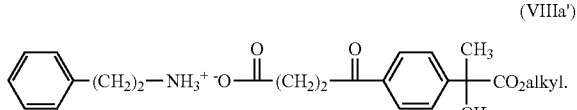
(VIIIa')

wherein alkyl is 1–6 carbon atoms.

8. The process according to claim 5 wherein the alkyl is methyl.

9. The process according to claim 5 wherein the alkyl is ethyl.

* * * * *